United States Patent [19]

Gardon et al.

[11] Patent Number: 5,175,227

[45] Date of Patent: * Dec. 29, 1992

[54] ACID ETCH RESISTANT COATINGS CONTAINING POLYURETHANE POLYOLS

[75] Inventors: John L. Gardon, Birmingham; Peter W. Uhlianuk, Armada; Scott W. Loper, West Bloomfield, all of Mich.

[73] Assignee: Akzo N.V., Arnhem, Netherlands

[*] Notice: The portion of the term of this patent subsequent to Oct. 13, 2009 has been disclaimed.

[21] Appl. No.: 517,091

[22] Filed: May 1, 1990

Related U.S. Application Data

[63] Continuation-in-part of Ser. No. 379,300, Jul. 13, 1989, abandoned.

[51] Int. Cl.$^5$ .............................................. C08G 18/81
[52] U.S. Cl. .................................... 528/45; 528/60; 528/61; 528/65; 528/85; 528/266; 528/423; 525/509
[58] Field of Search .................... 525/509; 528/45, 60, 528/61, 65, 85, 266, 423

[56] References Cited

U.S. PATENT DOCUMENTS

| | | | |
|---|---|---|---|
| 3,248,373 | 4/1966 | Barringer | 260/77.5 |
| 3,626,023 | 12/1971 | Brizyys | 117/124 |
| 3,785,861 | 1/1974 | Tanimura et al. | 171/138.8 B |
| 4,017,556 | 4/1977 | Wang | 427/421 |
| 4,021,505 | 5/1977 | Wang | 427/421 |
| 4,216,343 | 8/1980 | Rogier | 568/853 |
| 4,229,562 | 10/1980 | Rogier | 528/85 |
| 4,268,684 | 5/1981 | Gurgiolo | 560/24 |
| 4,284,750 | 8/1981 | Amirsakis | 528/79 |
| 4,288,577 | 9/1981 | McShane | 525/453 |
| 4,289,813 | 9/1981 | Blomeyer et al. | 427/395.5 |
| 4,410,667 | 10/1983 | Porter, Jr. et al. | 525/440 |
| 4,451,622 | 5/1984 | DiDomenico | 525/456 |
| 4,484,994 | 11/1984 | Jacobs, III et al. | 204/181 |
| 4,485,228 | 11/1984 | Chang et al. | 528/84 |
| 4,520,167 | 5/1985 | Blank et al. | 525/131 |
| 4,524,192 | 6/1985 | Alexander et al. | 525/440 |
| 4,530,976 | 7/1985 | Kordomenos et al. | 525/440 |
| 4,533,703 | 8/1985 | Kordomenos et al. | 525/440 |
| 4,533,704 | 8/1985 | Alexander et al. | 525/440 |
| 4,540,766 | 9/1985 | Chang et al. | 528/45 |
| 4,540,771 | 9/1985 | Ambrose et al. | 528/272 |
| 4,543,405 | 9/1985 | Ambrose et al. | 528/78 |
| 4,548,998 | 10/1985 | Chang et al. | 525/441 |
| 4,554,188 | 11/1985 | Holubka et al. | 427/393.5 |
| 4,559,383 | 12/1985 | Holubka et al. | 524/542 |
| 4,587,323 | 5/1986 | Toman | 528/66 |
| 4,605,724 | 8/1986 | Ambrose et al. | 528/73 |
| 4,631,320 | 12/1986 | Parekh et al. | 525/452 |
| 4,789,718 | 12/1988 | Noll et al. | 528/49 |

FOREIGN PATENT DOCUMENTS

| | | |
|---|---|---|
| 0139513 | 5/1985 | European Pat. Off. . |
| 0257848 | 3/1988 | European Pat. Off. . |
| 2611782 | 9/1976 | Fed. Rep. of Germany . |
| 144432 | 12/1976 | Japan . |
| 5-9006209A | 1/1984 | Japan . |
| 6-3089574A | 3/1988 | Japan . |

OTHER PUBLICATIONS

Sebenik, A. et al, "Study of the Reaction between Ethylene Glycol or 1,2-Propylene Glycol with Diphenylmethane-4,4'-diisocyanate," *J. Macromol. Sci-Chem.*, A20(3) (1983), pp. 341-353.

Primary Examiner—Maurice J. Welsh
Assistant Examiner—Rachel Johnson
Attorney, Agent, or Firm—James K. Poole; Louis A. Morris; Bart E. Lerman

[57] ABSTRACT

A high solids coating composition suitable for use, for example, as a high performance automotive coating is provided, which comprises (1) a particular polyurethane polyol which is the reaction product of an asymmetric diol component and an isocyanate component, and (2) an hydroxyl groups-reactive crosslinking agent. When formulated as a one-pack coating preferably with an aminoplast crosslinking agent, these coating compositions possess a number of desirable properties including excellent acid etch resistance.

29 Claims, No Drawings

ACID ETCH RESISTANT COATINGS CONTAINING POLYURETHANE POLYOLS

REFERENCES TO RELATED APPLICATIONS

This application is a continuation-in-part of application Ser. No. 07/379,300, filed Jul. 13, 1989, now abandoned. This application is related to commonly assigned and co-pending applications Ser. No. 07/517,086, filed May 1, 1990 and Ser. No. 07/640,655, filed Jan. 14, 1991, allowed Jul. 14, 1992, as U.S. Pat. No. 5,136,405.

BACKGROUND OF THE INVENTION

The present invention relates generally to high solids coating compositions suitable for use, for example, as high performance automotive coatings.

Many of the high performance, high solids automotive coatings presently in use are based upon polymeric systems comprised of either polyester-based or polyacrylic-based polyols and crosslinking agents therefor. These coatings are generally supplied as "one-pack" or "two-pack" systems.

In a typical one-pack system, all of the coating ingredients are combined into one storage stable mixture. Upon application the polyol component is crosslinked, generally with an aminoplast resin (such as a melamine resin) or a blocked isocyanate, under heat cure conditions of 120° C. or above. In a typical two-pack system, the polyol component is combined with a crosslinking agent, generally an isocyanate, shortly before application, with curing being conducted at ambient or elevated temperatures.

For environmental reasons, it is becoming increasingly important to develop polymeric systems with low solution viscosities, which permit the formulation of high solids coatings with low application viscosities suitable for spraying. High solids coatings (generally about 50 wt % or greater solids) significantly decrease the amount of volatile organic compounds (VOC) entering the atmosphere upon drying/curing of the coating.

To achieve acceptable solution viscosities (20-30 seconds, #4 Ford Cup at 20° C.) for typical high solids coating systems, the polyols should possess a weight average molecular weight (Mw) of about 5000 or lower. In general, the lower the Mw the lower the solution viscosity.

To achieve good film properties it is important that, upon film formation, the polyol molecules become sufficiently chemically bonded to each other. This can be accomplished by providing each polyol molecule with at least two reactive hydroxyl groups. A too low hydroxyl equivalent weight (HEW) (e.g., below about 200), however, may lead to brittle films. It has been found that, in general, the best spectrum of film properties may be obtained for HEWs between about 300 to 500. It follows, therefore, that for good film formation the polyols should possess a number average molecular weight (Mn) of at least about 800.

As is evident from the above discussion, the requirements for acceptable solution viscosities and good film properties lead to contradictory molecular weight requirements—for low solution viscosities the Mw should be low, but for good film properties the Mn should be high.

In acrylic free radical polymerization and in polycondensation leading to polyesters, it is difficult to achieve desirable molecular weights with sufficiently narrow molecular weight distributions. In other words, it is difficult to formulate high solids, high performance coating systems from acrylic and/or polyester based polyols which possess both acceptable application viscosities and resulting film properties.

A considerable amount of work in this area has recently been done relating to high solids, high performance coatings which are based, in part, upon relatively low molecular weight polyesterurethane, urethane-modified polyester and polyurethane polyols.

For example, U.S. Pat. Nos. 4,485,228, 4,540,766, 4,540,771 and 4,605,724 describe high solids coating systems based, in part, upon relatively low molecular weight polyesterurethane polyols and crosslinking agents therefor. More particularly, U.S. Pat. No. 4,485,228 describes a two-pack system with a polyisocyanate crosslinker, while U.S. Pat. No. 4,540,766 describes a one-pack system with an aminoplast or blocked isocyanate crosslinker. The polyesterurethane polyols of these references are produced via the reaction of a polyisocyanate with a stoichiometric excess of a polyester polyol.

In related U.S. Pat. No. 4,543,405 are disclosed high solids coatings based upon low molecular weight polyurethane polyols and/or higher molecular weight prepolymers (e.g., urethane-modified polyesters), which polyurethane polyols are produced by reacting a polyisocyanate with a large excess of a polyol. After completion of the reaction, the excess polyol is removed, e.g., by distillation. Also relevant in this aspect is U.S. Pat. No. 4,288,577.

U.S. Pat. No. 4,548,998, like those references just mentioned, describes a high solids coating system based upon a polyesterurethane polyol, except that the polyesterurethane polyol is produced by isocyanate-free reaction of a polyester polyol, urea and a polyamine.

U.S. Pat. Nos. 4,524,192, 4,533,703, and 4,533,704 and EP-A-0139513 describe similar high solids coating systems which are based, in part, upon urethane-modified polyester polyols and crosslinking agents therefor. The urethane-modified polyester polyols are produced by reacting a urethane-modified diol component (from a diol and diisocyanate) with a diacid component and a second polyol including at least 5 wt. % triol.

As mentioned above, due to environmental concerns it is becoming increasingly important to reduce the VOC of coatings in general. Additionally, due to the current deterioration of the environment and, particularly, the proliferation of acid rain, it is also becoming increasingly important that such coatings, upon curing/drying, display improved acid etch resistance.

To obtain high solids while maintaining acceptable viscosity for spray application, the industry has tended to decrease the Mn of the acrylic and polyester based polyols and increase the amount of crosslinker. Many of the state-of-the-art high solids systems, especially the one-pack systems, utilize aminoplast resins (such as hexamethoxymelamine resins) as the crosslinker. Generally, however, as the amount of aminoplast resin is increased, the acid etch resistance of these coatings is compromised. It is believed that the ester bonds in acrylic/melamine or polyester/melamine coatings are weak points in the crosslinked network, and susceptible to acid catalyzed hydrolysis.

Others of the aforementioned systems, formulated as two-pack systems with isocyanate crosslinkers, provide better acid etch resistance; however, the use of isocyanates has a number of disadvatages. For example, these two-pack systems require special handling and storage operations to avoid human exposure to the toxic isocyanates. Further, the components can only be mixed shortly prior to use, often resulting in mixing errors which can adversely affect the quality of the resulting coating.

It would, therefore, also be advantageous to provide a one-pack, high solids system, especially one that is isocyanate free, which displays a good balance of physical and chemical properties and, especially, good acid etch resistance.

SUMMARY OF THE INVENTION

In accordance with the present invention, there is provided a particularly advantageous coating composition which, in its overall concept, comprises:

(1) a polyurethane polyol possessing a number average molecular weight in the range of from about 600 to about 3000 and a degree of dispersion in the range of from about 1.1 to about 3.5, comprising the reaction product of (A) a diol component selected from substantially monomeric, asymmetric diols wherein the hydroxyl groups are separated by 3 carbon atoms or less, and (B) an isocyanate component selected from n-functional polyisocyanates, wherein n is a number in the range of from 2 to 5; and (2) an hydroxyl groups-reactive crosslinking agent.

It should be noted that, as used herein, the term "polyurethane polyol" refers to a reaction product wherein the reactants (diol component and polyisocyanate component) are linked substantially only via urethane linkage. This is in contrast, for example, to the aforementioned polyesterurethane and urethane-modified polyester polyols, in which the reactants are linked via urethane as well as ester linkages.

These coating compositions in accordance with the present invention are particularly suitable as high solids clear and pigmented coatings having non-volatiles contents generally ranging from about 40 wt % to about 80 wt %. Even at these high non-volatiles contents, the coatings possess relatively low viscosities generally ranging from about 25 cps to about 300 cps (at 20° C.).

Further upon application and curing of the coating compositions, the resulting films possess a number of desirable properties such as good UV durability, chemical and weathering resistance and other properties making them particularly suitable for use, for example, in automotive, general industrial, plastics and decorative coatings applications.

These coating compositions find particular use in high solids, high performance one-pack automotive coatings formulated with aminoplast and blocked isocyanate crosslinking agents. It has been found that such one-pack coatings, especially those formulated with the aminoplast crosslinking agents, possess a surprisingly high acid etch resistance as well as good non-yellowing behavior.

These and other features and advantages of the present invention will be more readily understood by one skilled in the art from a reading of the following detailed description.

DETAILED DESCRIPTION OF THE PREFERRED EMBODIMENTS

As just mentioned, the coating compositions in accordance with the present invention comprise, in general, (1) a particular polyurethane polyol and (2) a crosslinking agent for the hydroxyl groups of the polyurethane polyol.

Suitable polyurethane polyols are those possessing an Mn ranging from about 600 to about 3000, preferably of about 2500 or less and greater than about 1000, and a degree of dispersion (Mw/Mn) ranging from about 1.1 to about 3.5, preferably less than about 2.5, and especially less than about 2.0, which comprise the reaction product of:

(A) a diol component selected from substantially monomeric, asymmetric diols wherein the hydroxyl groups are separated by 3 carbon atoms or less, and (B) an isocyante component selected from n-functional polyisocyantes, wherein n is a number in the range of from 2 to 5.

The isocyanate component is selected from n-functional isocyanates wherein n is a number ranging from 2 to 5, preferably from 2 to 4, and especially from 3 to 4. The isocyanate component may comprise a single such n-functional isocyanate or combinations thereof.

As specific examples of suitable n-functional isocyanates may be mentioned, for example, diisocyanates such as 1,6-hexane diisocyanate (commerically available, for example, under the trade designation HMDI from Mobay Chemical), isophorone diisocyanate (commercially available, for example, under the trade designation IPDI from Huels America Inc.), tetramethylxylene diisocyanate (commercially available, for example, under the trade designation m-TMXDI from American Cyanamid Co.), 2-methyl-1,5-pentane diisocyanate, 2,2,4-trimethyl-1,6-hexane diisocyanate, 1,12-dodecane diisocyanate and methylene bis(4-cyclohexyl isocyanate) (commercially available, for example, under the trade designation Desmodur W from Mobay Chemical); and higher functional isocyanates such as a biuret of 1,6-hexane diisocyanate (commercially available, for example, under the trade designation Desmodur N from Mobay Chemical), an isocyanurate of 1,6-hexane diisocyanate (commercially available, for example, under the trade designation Desmodur N-3390 from Mobay Chemical), an isocyanurate of isophorone diisocyanate (commercially available, for example, under the trade designation Desmodur Z-4370 from Mobay Chemical), a reaction product of tetramethylxylene diisocyanate and trimethylol propane (commercially available, for example, under the trade designation Cythane 3160 from American Cyanamid), and a reaction product of one mole of trimethylol propane and 3 moles of toluene diisocyanate (commercially available, for example, under the trade designation Mondur CB from Bayer).

Particularly preferred for use with the present invention are the biurets and/or isocyanurates of monomeric diisocyanates, especially 1,6-hexane diisocyanate. Isocyanurates are typically obtained by the cyclotrimerization of three moles of the diisocyanate, while biurets are typically obtained by the reaction of three moles of the diisocyanate with one mole of water. Also particularly preferred are the reaction products of monomeric diisocyanates with multi-functional alcohols having from 2 to 4 hydroxyl groups, and wherein the ratio of hydroxyl groups to isocyanate groups is from about 0.45 to about 0.55.

As also indicated above, the diol component is selected from substantially monomeric, asymmetric diols wherein the hydroxyl groups are seperated by three carbon atoms or less. By "asymmetric diol" is meant a diol possessing hydroxyl groups of a different order, for example, a primary hydroxyl group and a secondary hydroxyl group. In other words, the diol component should comprise diols having one hydroxyl group which is more reactive with an isocyanate group than the other hydroxyl group on the molecule. The diol component may comprise a single such monomeric, asymmetric diol or combinations thereof.

Preferred asymmetric diols are those possessing from 3-18, more preferably from 4-18 and especially from 4-10 carbon atoms: and a primary hydroxyl group, and especially a primary and a secondary hydroxyl group. As specific preferred examples of such may be mentioned 2-ethyl-1,3-hexane diol, 1,2-propane diol, 1,3-butane diol, 1,2-hexane diol, 1,2-octane diol, 1,2-decane diol and 2,2,4-trimethyl-1,3-pentane diol. Especially preferred are 2-ethyl-1,3-hexane diol, 1,2-hexane diol, 1,2-octane diol, 1,2-decane diol and 2,2,4-trimethyl-1,3-pentane diol.

The polyurethane polyols are produced by reacting the diol component (A) and the isocyanate component (B) in a manner so as to result in the aforementioned desired molecular weight properties.

Preferably, this may be accomplished by reacting the components, in substantially stoichiometric ratios, at a temperature of about 125° C. or less, optionally in the presence of a polyurethane catalyst. More specifically, the components should be reacted in an amount such that the ratio of the number of moles of the diol component to the number of isocyanate equivalents of the isocyanate component is in the range of from 0.8 to 1.2, preferably from 0.9 to 1.1, more preferably from 0.95 to 1.05, still more preferably from 0.98 to 1.02, and especially 1 (stoichiometric).

Of course, the relative amounts of polyol and isocyanate components will depend upon the functionality of the isocyanate component. Stated another way, for every 1 mole of the n-functional isocyanate, there should be reacted from 0.8 n to 1.2 n, preferably from 0.9 n to 1.1 n, more preferably from 0.95 n to 1.05 n, still more preferably from 0.98 n to 1.02 n, and especially n moles of the diol component.

The components are preferably reacted at a temperature of about 125° C. or less, more preferably ranging from about 15° C. to about 125° C. The components may also optionally be reacted in the presence of a polyurethane catalyst. Suitable polyurethane catalysts are conventional and may be utilized in conventional amounts. Of course, the particular choice of catalyst type and amount will be dictated based upon a number of factors such as the particular components and reaction conditions. These and other factors are well-known to those skilled in the art, who can make the proper choices accordingly.

In an alternative but less convenient process, similar polyurethane polyols may also be made commercially in a manner such as described in U.S. Pat. No. 4,543,405 (see, for example column 6, line 52 through column 7, line 55), which is hereby incorporated by reference for all purposes. More specifically, the polyurethane polyols are produced by reacting, under generally standard polyurethane reaction conditions, the isocyanate component with a significant stoichiometric excess of the diol component. Upon completion of the reaction, the excess diol component is removed, for example, by distillation. Further details may be had by reference to U.S. Pat. No. 4,543,405.

Coating compositions may be formulated from these polyurethane polyols and suitable crosslinking agents. As suitable crosslinking agents may generally be mentioned any one of a number of well-known hydroxyl group-reactive crosslinking agents, such as polyisocyanates, blocked polyisocyanates and/or aminoplast resins.

The use of the above-described polyurethane polyols allows formulation of high solids coatings, possessing a non-volatiles content ranging from about 40 wt % to about 80 wt %, at low solutions ranging from about 25 cps to about 300 cps, preferably ranging from about 50 cps to about 200 cps, at 20° C.

As mentioned above, an especially advantageous use of the polyurethane polyols in accordance with the present invention is as a one-pack coating system formulated with an aminoplast and/or blocked polyisocyanate crosslinking agent, preferably an aminoplast crosslinking agent.

Generally speaking, the aminoplast crosslinking agents are aldehyde condensation products of melamine, urea, benzoguanamine or similar known compounds. The most commonly used aldehyde is formaldehyde. These condensation products contain methylol or similar alkylol groups, which are commonly etherified with an alcohol having from 1 to 4 carbon atoms, such as methanol or butanol. The aminoplast resin can be substantially monomeric or polymeric depending upon the desired end properties of the coating. For example, monomeric melamine resins are preferred because they allow coatings with higher solids contents, while polymeric melamines are useful in coatings where the use of a strong acid catalyst should be avoided.

As suitable specific examples of aminoplast crosslinkers of the type described above may be mentioned hexamethoxymethyl melamine (commercially available, for example, under the trade designation Cymel 303 from American Cyanamid); mixed ether methoxy/butoxy methylmelamines (commercially available, for example, under the trade designation Cymel 1135 from American Cyanamid), polymeric butoxy methylmelamine (commercially available, for example, under the trade designation M-281-M from Cook Paint and Varnish) and high imino polymeric methoxymethyl melamines (commercially available, for example, under the trade designation Cymel 325 from American Cyanamid). This list could include various other well-known crosslinkers which differ, for example, by degree of polymerization, imino content, free methylol content and ratios of alcohol used for etherification.

These aminoplast crosslinking agents may be utilized in widely varying weight ratios of polyurethane polyol to aminoplast, generally ranging from about 90:10 to 40:60, preferably from about 90:10 to 50:50.

As suitable isocyanate crosslinking agents may be mentioned any of a number of those known for use in similar systems. As specific examples may be mentioned the previously described n-functional isocyanates, especially the biuret and isocyanate versions. Blocking of such isocyanates is well-known to those skilled in the art and need not be detailed here.

As with the aminoplast crosslinking agents, the isocyanate crosslinking agents may also be utilized in widely varying amounts, but generally in equivalent ratios of hydroxyl to isocyanate groups ranging from about 0.7 to about 2.2.

The coating compositions may also contain a catalyst for the curing reaction, such as well-known acid catalysts and blocked derivatives thereof. Generally, these catalysts are utilized in amounts ranging from about 0.1% to about 5% by weight based upon the weight of the non-volatiles in the coating.

As specific examples of suitable acid catalysts may be mentioned phosphoric acid; alkyl acid phosphates such as phenyl acid phosphate; sulfonic acid and substituted sulfonic acids, such as p-toluene sulfonic acid (commercially available, for example, under the trade designation Cycat 4040 from American Cyanamid), amine blocked p-toluene sulfonic acid (commercially available, for example, under the trade designation VP-451 from Byk-Mallinckrodt), dodecylbenzene sulfonic acid (commercially available, for example, under the trade designation Bio-Soft S-100 from Stephan), amine blocked dodecylbenzene sulfonic acid (commercially available, for example, under the trade designations Nacure 5226 and Nacure XP-158 from King Industries) and dinonylnaphthalene disulfonic acid; and maleic acid and alkyl acid maleates.

Depending upon the field of application, the coating compositions may also contain a variety of other additives common to the paint industry such as solvents, pigments, coloring agents, pigment dispersing agents, light stabilizers, and thixotropic and other rheological agents.

Especially for pigmented systems, the coating compositions will normally be formulated to contain additives for flow, surface tension adjustment, pigment wetting and/or solvent popping. As examples of typical additives may be mentioned flow aids (commercially available, for example, under the trade designation A-620-A2 polybutylacrylate from Cook Paint and Varnish, and BYK-320 silicone from BYK-Mallinckrodt); pigment wetting aids (commercially available, for example, under the trade designation Disperbyk from BYK-Mallinckrodt); UV absorbers (commercially available, for example, under the trade designation Tinuvin 900 from Ciba-Geigy); and amine light stabilizers (commercially available, for example, under the trade designation Tinuvin 292 from Ciba-Geigy).

These coating compositions may be applied onto any number of wellknown substrates by any one of a number of conventional application methods. Curing of the coatings may be conducted under a variety of conditions, although curing of the above-described one-pack systems is preferably carried out under baking conditions, typically from about 80° C. to about 200° C.

The foregoing more general discussion of the present invention will be further illustrated by the following specific examples.

EXAMPLES (I) Synthesis of the Polyurethane Polyols

Polyurethane Polyol A

Into a 2 liter, 3 neck round bottom flask equipped with a stirrer, condensor, heating mantle, thermometer, dropping funnel and nitrogen inlet were charged the following:
438 g of 2-ethyl-1,3-hexane diol,
188 g of butyl acetate and
0.1 g of dibutyltin dilaurate,
and the mixture heated to 60° C. under a nitrogen blanket.

When the temperature had reached 60° C., the heating mantle was removed and the following mixture added over a 30 minute period:
648 g of the isocyanurate of hexamethylene diisocyanate (equivalent weight at 90% NV=216) (commercially available under the trade designation Desmodur N-3390 from Mobay Chemical) and
185 g of butyl acetate.

During addition of this mixture, the reaction temperature was kept below 70° C. After completion of the addition, the reaction temperature was held at 70° C. for 6 hours, at which point it was determined (by Fourier Transform Infared Spectroscopy-FTIR) that no residual isocyanate remained.

The resulting solution of polyurethane polyol A was a water white resin solution having a non-volatile content of 63.9% and a Brookfield viscosity of 1100 cps.

The molecular weights of the polymer were measured using a Waters Associates (Milford, Mass.) Model 840 Gel Permeation Chromatograph (GPC). The GPC was equipped with three 7.8 mm ID×30 cm ultrastyragel columns with linear, 100 and 500 angstrom pore sizes. A differential refractometer was used as a detector, and all samples were run using tetrahydrofuran (THF) as eluent with a flow rate of 1.0 ml/min.

Tp determine the molecular weights, a calibration curve was constructed using a combination of polystyrene (PS) standards (covering a high molecular weight range) and polyethylene glycol (PEG) standards (covering a low molecular weight range) obtained commercially from American Polymer Standards Corp. (Mentor, Ohio) The peak molecular weights (Mp) of the PS standards were 2070, 4000, 5450, 8500, 9300, 14,000, 20,600, 30,800, 49,000, 110,000, 240,000 and 390,000. The peak molecular weights of the PEG standards were 62, 106, 238, 330, 425, 610, 1050 and 1500.

To obtain the calibration curve, standard solutions were prepared from 0.1 g of a standard diluted to a total volume of 25 ml with THF. A claibration standard could contain up to four individual standards so long as each standard differed in Mp from all other standard in the solution by a 10-fold factor. The calibration standards were filtered through a 45 micron filter (commerically obtained from Phenomenex Inc., Torrence, Calif.), the 100 microliters of the solution was injected onto the columns and a chromatogram obtained. A calibration curve of elution time vs. log molecular weight using a narrow standard calibration and third order fit was obtained with the Waters Model 840 software, version 6.2.

The samples to be analyzed were prepared by placing 0.1 g of the sample in a 25 ml volumetric flask and diluting with THF. After filtration through the 45 micron filter, 100 microliters was injected onto the colums and a chromatogram obtained. The Mw, Mn and Mw/Mn were obtained relative to the above-described calibration curve using the Waters Model 840 software.

The polyurethane polyol A had an Mn of 1760, Mw of 2994 and degree of dispersion of 1.70.

Polyurethane Polyols B-E

Polurethane polyols B-E were produced in a similar manner to polyurethane polyol A, from the components as set forth in Table I.

TABLE I

| Reactants | Polyurethane Polyol | | | |
|---|---|---|---|---|
| | B (grams) | C (grams) | D (grams) | E (grams) |
| 2-ethyl-1,3-hexane diol | 876.0 | 876.0 | 499.4 | 930.0 |
| Methyl propyl ketone | 415.0 | 150.0 | 187.4 | 110.0 |
| Dibutyltin dilaurate | 0.2 | 0.2 | 0.1 | 0.2 |
| Methylene-bis(cyclohexyl isocyanate)[1] | 786.0 | — | — | — |

TABLE I-continued

| Reactants | Polyurethane Polyol | | | |
|---|---|---|---|---|
| | B (grams) | C (grams) | D (grams) | E (grams) |
| Isocyanurate of 1,6-hexane diisocyanate[2] | — | 1164.0 | — | — |
| Isocyanurate of 1,6-hexane diisocyanate[3] | — | — | 624.9 | — |
| Biuret of 1,6-hexane diisocyanate[4] | — | — | — | 1624.0 |
| Methyl propyl ketone | — | 360.0 | 187.4 | 200.0 |

[1] commercially available under the trade designation Desmodur W from Mobay Chemical.
[2] eq. weight 181, commercially available under the trade designation Tolonate HDT from Rhone-Poulenc.
[3] eq. weight 216 at 90% non-volatiles, commercially available under the trade designation Desmodur N-3300LV from Mobay Chemical.
[4] commercially available under the trade designation Desmodur N-75 from Mobay Chemical.

The diol, methyl propyl ketone and dibutyltin dilaurate were charged to a 5 liter flask and the mixture heated to 60° C. The isocyanate and additional methyl propyl ketone were then added to the flask over a period of 1-2 hours. After the addition, the reaction mixture was held at approximately 70° C. until no isocyanate was detected by FTIR, generally from 0.5 to 2 hours.

The properties of the resulting polyurethane polyols B-E and solutions are reported in Table II.

TABLE II

| Property | Polyurethane Polyol | | | |
|---|---|---|---|---|
| | B | C | D | E |
| Solutions | | | | |
| Non-volatile % | 78.0 | 78.1 | 71.1 | 75.7 |
| Brookfield viscosity (cps) | 4000 | 3500 | 1680 | 4000 |
| Polyols | | | | |
| OH number (mg KOH/g) | 202 | 168 | 170 | 165 |
| Mn | 687 | 1844 | 1613 | 2050 |
| Mw | 876 | 3594 | 2580 | 5020 |
| Degree of dispersion (Mw/Mn) | 1.28 | 1.95 | 1.60 | 2.45 |

(II) Formulation of Clear Coatings

Examples 1-2 and Comparative Examples 1-3

The polyurethane polyol A solution was utilized to formulate melamine crosslinked clear coatings at 30% (Example 1) and 45% (Example 2) by weight of a hexamethoxymethyl melamine ("HMMM") (commercially available under the trade designation Cymel 303 from American Cyanamid), based upon total resin solids.

For the sake of comparison, high solids, one pack coatings based upon a typical hydroxy functional polyacrylate were also formulated with 30% (Comparative Example 1) and 45% (Comparative Example 2) by weight levels of the HMMM crosslinker.

These examples were catalyzed with an amine blocked dodecylbenzene sulfonic acid catalyst (commercially available under the trade designation Nacure 5226 from King Industries) at 0.38% active catalyst based upon resin solids.

Generally speaking, the aforementioned hydroxy functional polyacrylate can be characterized as a standard commercial system produced from combinations of methyl methacrylate, butyl or ethyl acrylate, styrene, hydroxyethyl or hydroxypropyl acrylate or methacrylate, lactone-modified hydroxyethyl acrylate and traces of acrylic or methacrylic acid. The Mw of such standard polyacrylate polyol can range from 4000 to 10,000, the Mn from 2000 to 5000, the degree of dispersion from 2 to 4.5, the hydroxy equivalent weight from 330 to 560 (corresponding to OH numbers ranging from 100 to 170), the acid number from 0 to 25, and the glass transition temperature (Tg) from $-5°$ C. to $20°$ C.

Additionally tested was a high solids, two-pack coating based upon this same hydroxy functional acrylate and, as crosslinker, the isocyanurate of 1,6-hexane diisocyanate (commercially available under the trade designation Desmodur N-3390 from Mobay Chemical) (Comparative Example 3).

All samples were reduced to 60% non-volatiles by addition of butyl acetate, and then drawn down at 1.5-1.8 mils dry film thickness on aluminum test panels. The coatings were cured for 30 minutes at about 120° C. (250° F.).

The so-produced coatings were tested for acid etch resistance by application of a simulated acid rain solution formulated by mixing 1 normal aqueous solutions of sulfuric, nitric and hydrochloric acids at a volume ratio of 65/30/5, the resulting solution having a pH of 0.2.

Each panel was spotted with 0.5 ml of the above simulated acid rain solution and left standing uncovered at room temperature. Evaporated acid rain solution was replaced with additional solution at regular intervals (2 hours) so that the spot size remained the same throughout testing. At the end of the exposure time, the panel was rinsed with distilled water and allowed to dry overnight. The panels were inspected for damage the following day. The exposure times required to damage the various coatings are reported below in Table III.

TABLE III

| Example | Melamine Level | Hours to First Spot | Hours to Film Degradation |
|---|---|---|---|
| C1 | 30% | 4 | Not degraded after 7 hours |
| C2 | 45% | 2 | 4 |
| 1 | 30% | No spot after 7 hours | — |
| 2 | 45% | No spot after 7 hours | — |
| 3 | — | No spot after 7 hours | — |

These results suggest that a significant improvement in acid etch resistance was obtained by replacement of a standard acrylic polyol with a polyurethane polyol in accordance with the present invention. Further, the melamine crosslinked coatings based upon the polyurethane polyols in accordance with the present invention displayed acid etch resistance approaching that of a two-component acrylic urethane system known for its acid resistance.

Examples 4-8 and Comparative Examples 4-5

Polyurethane polyols A and D were formulated into melamine crosslinked clearcoats suitable for wet-on-wet application by spray over high solids, pigmented, melamine crosslinked basecoats. The basecoats and clearcoats were applied in two passes, with a 5-10 minute flash-off between applications.

Two melamine crosslinkers were evaluated at two different levels for each polyurethane polyol—an HMMM (commercially available under the trade designation Cymel 303 from American Cyanamid) at 30% (Example 4) and 40% (Examples 5 and 6) based upon resin solids, and a methylated-butylated mixed ether melamine ("MEMM") (commerically available under the trade designation Cymel 1135 from American Cyanamid) at 40% (Examples 7 and 8) based upon resin solids.

The acid catalyst utilized was the same as for Examples 1-2, at similar levels. Additionally, a flow additive was added to adjust the wetting properties of the clearcoats.

These clearcoats were applied wet-on-wet over the above-mentioned pigmented basecoat in two passes, with a 5-10 minute flash off between passes, on 20 gauge phosphated steel and cured for 30 minutes at 120° C. (250° F.). The dry film thickness of the cured clearcoats was approximately 1.6 mils.

These coatings were tested for acid etch resistance as described earli for Examples 1-2. Two panels coated with automobile industry (OEM) standard melamine crosslinked basecoat/clearcoat systems were utilized for comparison (Comparative Examples 4 and 5). The results are presented below in Table IV.

TABLE IV

| Example | Polyurethane Polyol | Melamine Type | Melamine Level | Hours to First Spot |
|---|---|---|---|---|
| 4 | A | HMMM | 30% | 12 |
| 5 | A | HMMM | 40% | 11 |
| 6 | D | HMMM | 40% | 10 |
| 7 | A | MEMM | 40% | 11 |
| 8 | D | MEMM | 40% | 12 |
| C4 | | | | 4 |
| C5 | | | | 5 |

Example 9

A one-pack clearcoat was formulated from the following components, which were blended utilizing equipment and techniques commonly utilized in the coatings industry:
164 parts by weight of the polyurethane D solution,
74 parts by weight of an HMMM (commercially available under the trade designation Cymel 303 from American Cyanamid),
1.4 parts by weight of a blocked acid catalyst (commercially available under the trade designation Nacure 5226 from King Industries) and
72 parts by weight of methyl amyl ketone.

The clearcoat was applied wet-on-wet over a waterborne basecoat, in a manner described above, using air atomized hand spray guns. After application, the system was cured by baking in an oven for a period of about 30 minutes at about 120° C. (250° F.). The resulting clearcoat thickness was about 1.6 mils.

The cured film properties of the clearcoat were measured as follows: hardness was about 15 knoops (as measured by a Tukon Tester); gloss was about 88 at 20° (as measured by a BYK-Mallincroft Meter); and distinctness of image was about 92 units (as measured by a Model 1792 DOI Meter supplied by A.T.I. Systems).

Acid etch resistance was tested as in Examples 1-2 at ambient temperature (about 20° C.) No visible effect of the acid exposure was observed until after 10 hours.

Such excellent acid resistance must be considered unexpected in view of the fact that the typical commercial, one-pack, high solids, automotive, acrylic clearcoat, applied and tested under the same conditions was visibly affected after just 3-4 hours.

Similar excellent acid resistance results were observed when the above polyurethane polyol based clearcoat was similarly applied over typical commercial, high solids, automotive, one-pack and two-pack acrylic basecoats.

(III) Formulation of Pigmented Coatings

Example 10

A single layer pigmented top coat was prepared as follows.

Into a mixing vessel were placed 150 parts by weight of the polyurethane polyol D solution, to which was added 183 parts by weight of a titanium dioxide pigment (commercially available under the trade designation Titanox 2160 from NL Chemicals). These components were blended using high speed dispersion equipment.

After dispersion of the pigment, the following were added:
106 parts by weight of the HMMM crosslinker of Example 8,
53 parts by weight butyl acetate,
12 parts by weight of the blocked acid catalyst of Example 8,
96 parts by weight of methyl amyl ketone and
150 additional parts by weight of the polyurethane polyol D solution.

The non-volatile content of the so-produced coating was 65.0% by weight.

The topcoat was applied to 20 gauge phosphated steel test panels and cured as in Example 8, resulting in a cured coating layer thickness of 2.0 mils.

The cured film properties were measured as in Example 8: hardness was about 14 knoops; gloss was about 87; and distinctness of image was about 80 units.

Acid etch resistance was tested as in Examples 1-2 at ambient temperature (about 20° C.). No visible effect of the acid exposure was observed until after 7 hours.

Again such excellent acid resistance must be considered unexpected in view of the fact that typical acrylic, high solids, one-pack automotive topcoats with about the same pigment content (i.e., the same hiding power), applied and tested under the same conditions, were visibly affected after just 2 hours.

Only a limited number of preferred embodiments of the present invention have been described above. One skilled in the art, however, will recognize numerous substitutions, modifications and alterations which can be made without departing from the spirit and scope of the invention as limited by the following claims.

We claim:
1. A coating composition comprising:
   (1) a polyurethane polyol possessing a number average molecular weight in the range of from about 600 to about 3000 and a degree of dispersion in the range of from about 1.1 to about 3.5, comprising the reaction product of (A) a diol component selected from substantially monomeric, asymmetric diols wherein the hydroxyl groups are separated by 3 carbon atoms or less, and (B) an isocyanate component selected from n-functional polyisocyanates, wherein n is a number in the range of from 2 to 5; and
   (2) an hydroxyl groups-reactive crosslinking agent.
2. The coating composition of claim 1, possessing a non-volatiles content ranging from about 40 wt % to about 80 wt % at a solution viscosity ranging from about 25 cps to about 300 cps at 20° C.
3. The coating composition of claim 2, possessing a non-volatiles content ranging from about 40 wt % to about 80 wt % at a solution viscosity ranging from about 50 cps to about 200 cps at 20° C.

4. The coating composition of claim 1, wherein the polyurethane polyol comprises the reaction product of (A) from 0.8 n to 1.2 n moles of the diol component and (B) 1 mole of the isocyanate component.

5. The coating composition of claim 4, wherein the polyurethane polyol comprises the reaction product of (A) from 0.9 n to 1.1 n moles of the polyol component, and (B) 1 mole of the isocyanate component.

6. The coating composition of claim 5, wherein the polyurethane polyol comprises the reaction product of (A) from 0.95 n to 1.05 n moles of the polyol component, and (B) 1 mole of the isocyanate component.

7. The coating composition of claim 6, wherein the polyurethane polyol comprises the reaction product of (A) from 0.98 n to 1.02 n moles of the polyol component, and (B) 1 mole of the isocyanate component.

8. The coating composition of claim 1, wherein n is a number in the range of from 2 to 4.

9. The coating composition of claim 8, wherein n is a number in the range of from 3 to 4.

10. The coating composition of claim 9, wherein the polyisocyanate component of the polyurethane polyol is selected from an isocyanurate of a monomeric diisocyanate, a biuret of a monomeric diisocyanate, and the reaction product of a monomeric diisocyanate with a multi-functional alcohol having 2 to 4 hydroxyl groups in a ratio of hydroxyl to isocyanate groups of from about 0.45 to 0.55.

11. The coating composition of claim 1, wherein the diol component of the polyurethane polyol is selected from substantially monomeric asymmetric diols having a primary and a secondary hydroxyl group.

12. A coating composition comprising:
(1) a polyurethane polyol possessing a number average molecular weight in the range of from about 600 to about 3000 and a degree of dispersion in the range of from about 1.1 to about 3.5, comprising the reaction product of (A) a diol component selected from substantially monomeric, asymmetric diols having a primary and a secondary hydroxyl group wherein the hydroxyl groups are separated by 3 carbon atoms or less, and (B) an isocyanate component selected from n-functional polyisocyanates, wherein n is a number in the range of from 2 to 5; and
(2) an hydroxyl groups-reactive crosslinking agent, wherein the diol component of the polyurethane polyol is selected from 2-ethyl-1,3-hexane diol, 1,2-propane diol, 1,3-butane diol, 1,2-hexane diol, 1,2-octane diol, 1,2-decane diol and 2,2,4-trimethyl-1,3-pentane diol.

13. The coating composition of claim 12, wherein the polyol component of the polyurethane polyol is selected from 2-ethyl-1,3-hexane diol, 1,2-hexane diol, 1,2-octane diol, 1,2-decane diol and 2,2,4-trimethyl-1,3-pentane diol.

14. The coating composition of claim 1, wherein the polyurethane polyol possesses a number average molecular weight of about 2500 or less.

15. The coating composition of claim 1, wherein the polyurethane polyol possesses a number average molecular weight greater than about 1000.

16. The coating composition of claim 1, wherein the polyurethane polyol possesses a degree of dispersion of about 2.5 or less.

17. The coating composition of claim 16, wherein the polyurethane polyol possesses a degree of dispersion of about 2.0 or less.

18. The coating composition of claim 1, wherein the hydroxyl groups-reactive crosslinking agent is at least one agent selected from the group consisting of polyisocyanates, blocked polyisocyanates and aminoplast resins.

19. The coating composition of claim 18, wherein the hydroxyl groups-reactive crosslinking agent comprises an aminoplast resin.

20. The coating composition of claim 19, wherein the hydroxyl groups-reactive crosslinking agent comprises an aminoplast resin in a weight ratio of polyurethane polyol to aminoplast resin in the range of from about 90:10 to 50:50.

21. The coating composition of claim 20, wherein the aminoplast resin comprises an hexamethylol melamine etherified with an alcohol having from 1 to 4 carbon atoms.

22. The coating composition of claim 19, formulated as a one-pack system.

23. The coating composition of claim 22, possessing a non-volatiles content ranging from about 40 wt % to about 80 wt % at a solution viscosity ranging from about 25 cps to about 300 cps at 20° C.

24. The coating composition of claim 23, possessing a non-volatiles content ranging from about 40 wt % to about 80 wt % at a solution viscosity ranging from about 50 cps to about 200 cps at 20° C.

25. The coating composition of claim 1 wherein said diol component contains from 4 to about 10 carbon atoms.

26. The coating composition of claim 1 wherein said diol is a substituted or unsubstituted 1,2 or 1,3 aliphatic diol having from 3 to about 18 atoms.

27. The coating composition of claim 13 wherein said isocyanate component comprises an isocyanurate of a monomeric diisocyanate and said crosslinking agent comprises an hexamethoxymethylmelamine.

28. The coating composition of claim 18 wherein said crosslinking agent comprises a polyisocyanate or blocked polyisocyanate.

29. A coating composition comprising:
(1) a polyurethane polyol possessing a number average molecular weight in the range of from about 600 to about 3000 and a degree of dispersion in the range of from about 1.1 to about 3.5, comprising the reaction product of
(A) a diol component selected from substantially monomeric, asymmetric diols having from 3 to 18 total carbon atoms, wherein the hydroxyl groups are separated by 2 or 3 carbon atoms, and
(B) an isocyanate component selected from n-functional polyisocyanates, wherein n is a number in the range of from 3 to 4; and
(2) an hydroxyl group-reactive crosslinking agent selected from the group consisting of polyisocyanates and blocked polyisocyanates.

* * * * *